United States Patent
Hayashi et al.

(10) Patent No.: US 10,487,034 B2
(45) Date of Patent: Nov. 26, 2019

(54) ALKYLATED DIPHENYL ETHER COMPOUND AND LUBRICATING OIL CONTAINING SAID COMPOUND

(71) Applicant: MORESCO CORPORATION, Kobe-shi, Hyogo (JP)

(72) Inventors: Mayumi Hayashi, Kobe (JP); Shingo Maruyama, Kobe (JP)

(73) Assignee: MORESCO CORPORATION, Kobe-shi (JP)

(*) Notice: Subject to any disclaimer, the term of this patent is extended or adjusted under 35 U.S.C. 154(b) by 117 days.

(21) Appl. No.: 14/401,955

(22) PCT Filed: Oct. 30, 2013

(86) PCT No.: PCT/JP2013/080056
§ 371 (c)(1),
(2) Date: Nov. 18, 2014

(87) PCT Pub. No.: WO2014/069669
PCT Pub. Date: May 8, 2014

(65) Prior Publication Data
US 2015/0166447 A1    Jun. 18, 2015

(30) Foreign Application Priority Data
Oct. 31, 2012  (JP) .................... 2012-240337

(51) Int. Cl.
*C07F 5/04* (2006.01)
*C10M 105/18* (2006.01)
*C07C 43/275* (2006.01)

(52) U.S. Cl.
CPC ......... *C07C 43/275* (2013.01); *C10M 105/18* (2013.01)

(58) Field of Classification Search
CPC .................. C10M 129/16; C10M 2207/04
(Continued)

(56) References Cited

U.S. PATENT DOCUMENTS 5,552,071 A * 9/1996 Rudnick ................ C07C 15/16
                                                        508/581
2008/0085847 A1* 4/2008 Tse ....................... C10M 143/00
                                                        508/591
(Continued)

FOREIGN PATENT DOCUMENTS

JP        58-22515 B2    5/1983
JP        2572814 B2     1/1997
(Continued)

OTHER PUBLICATIONS

International Search Report dated Feb. 10, 2014 issued in corresponding application No. PCT/JP2013/080056.
(Continued)

*Primary Examiner* — Prem C Singh
*Assistant Examiner* — Francis C Campanell
(74) *Attorney, Agent, or Firm* — Westerman, Hattori, Daniels & Adrian, LLP

(57) ABSTRACT

A compound of the formula (2)

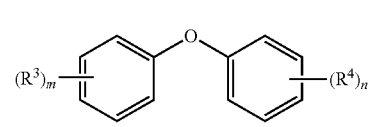

(2)

wherein $R^3$ is a hydrocarbon group having 12 or 14 carbon atoms which is mainly composed of any one of 1-methylundecyl, 1-ethyldecyl, 1-dodecyl, 1-methyltridecyl, 1-ethyldodecyl and 1-tetradecyl, and 30 to 40 mole % of the total benzylic carbons of $R^3$ being quaternary, $R^4$ is a branched hydrocarbon group having 16 to 20 carbon atoms, 42 to 100
(Continued)

mole % of the total benzylic carbons of each $R^3$ and $R^4$ being quaternary, m and n are each a real number of $1.0 \leq m \leq 2.0$, $1.0 \leq n \leq 2.0$ and $2.0 \leq m+n \leq 3.0$.

13 Claims, 6 Drawing Sheets

(58) Field of Classification Search
USPC .................................................. 508/581
See application file for complete search history.

(56) References Cited

U.S. PATENT DOCUMENTS

| | | | |
|---|---|---|---|
| 2008/0234157 A1* | 9/2008 | Yoon | C10M 105/06 508/591 |
| 2015/0225327 A1* | 8/2015 | Hayashi | C07C 43/275 508/581 |

FOREIGN PATENT DOCUMENTS

| | | |
|---|---|---|
| JP | 2000-345178 A | 12/2000 |
| JP | 2007-332240 A | 12/2007 |
| JP | 2008-208174 A | 9/2008 |
| JP | 2010-522258 A | 7/2010 |
| JP | 2012-102051 A | 5/2012 |

OTHER PUBLICATIONS

Kono, "Practical examples and effects of phenyl ether-based synthetic lubricants", Lubrication Economy, vol. 417, Dec. 5, 2000, pp. 18-23; cited in the Specification.

Nozaki et al., "Technical trend of bearing for electric auxiliary machine", NTN Technical Review, No. 65, 1996, pp. 65-72; cited in the Specification.

* cited by examiner

ALKYLATED DIPHENYL ETHER COMPOUND AND LUBRICATING OIL CONTAINING SAID COMPOUND

TECHNICAL FIELD

The present invention relates to a diphenyl ether compound substituted with hydrocarbon group, a lubricant containing the compound for high temperature use and a heat-resistant grease.

BACKGROUND ART

In recent years, lubricants such as lubricating oil or lubricating grease are used under a severe condition such as high temperature, high speed and high load with downsizing and lightweighting of various machines and bearings, high speed processing and maintenance-free systems. Therefore, lubricants are become indispensable which have superior heat resistance and oxidation resistance.

In bearing lubrication, under high temperature and high-speed condition, a lubricating oil or grease used for lubrication causes a temperature increase due to oil film shortage or heat and oxidative degradation. As a result, a base oil of lubricant is promoted to evaporate to form sludge, damage the bearing and decrease a life of machine.

Therefore, various lubricating oils and greases are investigated which are usable at high temperature condition. Generally, an improvement of the lubricants under a high temperature condition highly depends on a base oil of lubricant which is contained at largest amount. Examples of such heat-resistant base oils are polyphenyl ether, silicone oil and fluorinate oil (for example, non-patent literature 2). However, polyphenyl ether and fluorinated oil are generally very expensive, and silicone oil is said to be generally disadvantageous in lubricity.

It is important to take a balance between cost and performance of the base oil for providing lubricating oils and greases which are low-cost but high-performance. Lubricating oil for high temperatures and heat-resistant grease are known which use alkyl diphenyl ether as a base oil (e.g., HILUBE LB-100, MORESCO Corporation) (for example, patent literatures 1 and 2, non-patent literature 1). Alkyl diphenyl ether is excellent in stability to heat and oxidation, causes particularly a little evaporation in use under high temperature, and small in viscosity variation. Further, when heat-resistant grease containing alkyl diphenyl ether as a base oil is used for a ball bearing and a roller bearing, it is apparent that brittle separation by hydrogen brittleness of metal materials extremely decreases which is caused by invasion of hydrogen to the steel which occurs in fixed rings (for example, non-patent literature 2). Because such a characteristic is hardly available by other general-purpose synthetic lubricants, e.g., α-olefin oligomer, polyalkylene glycols, ester-based oil, a heat-resistant grease lubricating oil which is relatively inexpensive and superior property can be obtained using alkyl diphenyl ether.

With the above superior property, a heat-resistant grease using the alkyl diphenyl ether as a base oil can be used in a wide temperature range from low to high temperatures, and is widely used for a bearing for automobile electric auxiliary machine such as an alternator which requires long life and long-term reliability.

However, in recent years, these automobile electric auxiliary parts become inferior in thermal dissipation due to downsizing and lightweighting of the parts. Therefore, the heat-resistant grease for bearing is used under more severe condition than usual in view of temperature environment, and more improvement of the base oil is expected.

At present, alkyl diphenyl ether is prepared by an addition reaction of diphenyl ether and a linear α-olefin such as 1-dodecene or 1-tetradecene, and a ratio of the carbon at benzyl position being quaternary is 30 to 40 mole %. This alkyl diphenyl ether is expected to be more improved in heat-resistance. Further, alkyl diphenyl ether is expected which is equal in flowability at low temperature to the current alkyl diphenyl ether.

PRIOR ART LITERATURE

Patent Literature 1: JP 1983-22515B
Patent Literature 2: JP Patent No. 2572814
Non-patent Literature 1: Masatsugu Kono, Practical examples and effects of phenyl ether-based synthetic lubricants, Lubrication Economy, Dec. 5, 2000, Vol. 417 (December 2000), p 18-23
Non-patent Literature 2: Seiichi Nozaki et al, Technical trend of bearing for electric auxiliary machine, NTN TECHNICAL REVIEW, No. 65 (1996), p 65-72

SUMMARY OF THE INVENTION

Problem to be Solved by the Invention

An object of the present invention is to provide an alkyl diphenyl ether which maintains flowability at low temperature of the conventional alkyl diphenyl ether and superior heat stability (particularly less susceptible to be oxidized by heat) when used as a base oil for various lubricants such as lubricating oil or grease.

Means for Solving the Problem

The present invention provides the following compound and lubricant.

1. A compound of the formula (2)

(2)

wherein $R^3$ is a hydrocarbon group having 12 or 14 carbon atoms which is mainly composed of any one of 1-methylundecyl, 1-ethyldecyl, 1-dodecyl, 1-methyltridecyl, 1-ethyldodecyl and 1-tetradecyl, and 30 to 40 mole % of the total benzylic carbons of $R^3$ being quaternary, $R^4$ is a branched hydrocarbon group having 16 to 20 carbon atoms, 42 to 100 mole % of the total benzylic carbons of each $R^3$ and $R^4$ being quaternary, m and n are each a real number of $1.0 \leq m \leq 2.0$, $1.0 \leq n \leq 2.0$ and $2.0 \leq m+n \leq 3.0$. A benzylic carbon refers to a carbon in an alpha position next to a phenyl ring.

2. A compound of the formula (2) obtained by an addition reaction of diphenyl ether derivative of the formula (3) and a branched α-olefin of the formula (1) or its corresponding branched alkyl halide (3)

-continued wherein R$^1$ and R$^2$ are the same or different and are a hydrocarbon group having 4 to 12 carbon atoms, R$^3$, R$^4$, m and n are same as above.

3. A compound of the formula (2) as defined in any one of the above items 1 to 2 wherein the total of a ratio of the carbon at benzyl position of each R$^3$ and R$^4$ being quaternary is 45 to 95 mole %.

4. A compound of the formula (2) as defined in any one of the above items 1 to 2 wherein 50 to 90 mole % of the total benzylic carbons of each R$^3$ and R$^4$ is quaternary.

5. A compound of the formula (2) as defined in any one of the above items 1 to 2 wherein 50 to 65 mole % of the total benzylic carbons of each R$^3$ and R$^4$ is quaternary.

6. A compound of the formula (2) as defined in any one of the above items 1 to 5 wherein R$^4$ is 1-butyl-1-methylheptyl, 1-methyl-1-pentyloctyl, 1-hexyl-1-methylnonyl, 1-heptyl-1-methyldecyl, 1-methyl-1-octylundecyl or 1-decyl-1-methyltridecyl.

7. A lubricating oil which is usable at high temperature containing a compound of the formula (2)

wherein R$^3$, R$^4$, m and n are same as above.

8. A heat-resistant grease containing a compound of the formula (2)

wherein R$^3$, R$^4$, m and n are same as above.

Effects of the Invention

The compound of the present invention exhibits equal flowability at low temperature to the conventional, well known and practically used alkyl diphenyl ether, small evaporation loss at high temperature and excellent stability to oxidation. Therefore, the present compound is usable as a base oil for lubricants such as lubricating oil or heat-resistant grease usable at further high temperature.

Embodiment of Practicing the Invention

The present invention provides a compound of the formula (2)

wherein R$^3$ is a hydrocarbon group having 12 or 14 carbon atoms which is mainly composed of any one of 1-methylundecyl, 1-ethyldecyl, 1-dodecyl, 1-methyltridecyl, 1-ethyldodecyl and 1-tetradecyl, and 30 to 40 mole % of the total benzylic carbons of R$^3$ being quaternary, R$^4$ is a branched hydrocarbon group having 16 to 20 carbon atoms, 42 to 100 mole % of the total benzylic carbons of each R$^3$ and R$^4$ being quaternary, m and n are each a real number of 1.0≤m≤2.0, 1.0≤n≤2.0 and 2.0≤m+n≤3.0.

The compound of the formula (2) of the present invention is obtained by an addition reaction of diphenyl ether derivative of the formula (3) and a branched α-olefin of the formula (1) or its corresponding branched alkyl halide wherein R$^1$ and R$^2$ are the same or different and are a hydrocarbon group having 4 to 12 carbon atoms, R$^3$, R$^4$, m and n are same as above.

In the compound of the formula (1), R$^1$ and R$^2$ are the same or different and are a hydrocarbon group having 4 to 12 carbon atoms. Examples thereof are butyl, hexyl, octyl, decyl and dodecyl. R$^1$ and R$^2$ are preferably hydrocarbon group having 6 to 10 carbon atoms.

A compound of the formula (1a) can be used as a compound of the formula (1)

wherein r is an integer of 2 to 10, preferably 4 to 8.

Examples of compound of the formula (1) are 2-butylhexene, 2-butyloctene, 2-pentylnonene, 2-hexyloctene, 2-hexyldecene, 2-octyldecene, 2-octyldodecene, 2-decyldodecene, 2-decyltetradecene and 2-dodecylhexadecene.

Examples of compound of the formula (1a) are 2-butyloctene, 2-pentylnonene, 2-hexyldecene, 2-heptylundecene, 2-octyldodecene and 2-decyltetradecene.

In the compound of the formula (2), R$^3$ is a hydrocarbon group having 12 or 14 carbon atoms which is mainly composed by any one of 1-methylundecyl, 1-ethyldecyl, 1-dodecyl, 1-methyltridecyl, 1-ethyldodecyl and 1-tetradecyl, and 30 to 40 mole % of the total benzylic carbons of being quaternary, $R^4$ is a branched hydrocarbon group having 16 to 20 carbon atoms, 42 to 100 mole % of the total benzylic carbons of each $R^3$ and $R^4$ being quaternary, m and n are each a real number of $1.0 \leq m \leq 2.0$, $1.0 \leq n \leq 2.0$ and $2.0 \leq m+n \leq 3.0$.

Examples of $R^3$ are the following hydrocarbon groups.

Examples of $R^4$ are the following branched hydrocarbon groups.

In the compound of the formula (2) of the present invention, when $R^4$ is less than 16 in carbon number, excess amount of evaporation occurs, and when more than 20 in carbon number, viscosity and pour point are too high. The hydrocarbon groups $R^3$ and $R^4$ may bond to any position of any of two aromatic rings of diphenyl ether. $R^4$ is preferably hydrocarbon group having 16 to 20 carbon atoms.

The compound of the formula (2) of the present invention can be prepared by, for example, Friedel-Crafts reaction of diphenyl ether derivative of the formula (3) with branched α-olefin or its corresponding branched alkyl halide using aluminum chloride as a catalyst. Alkyl diphenyl ether wherein di- or more alkylated diphenyl ether is contained as a main component can be obtained by removing low-boiling compounds such as an unreacted starting compound or diphenyl ether derivative of the formula (3) by distillation or the like.

In the following, the present process is explained in more detail with showing an example.

A catalyst is added to diphenyl ether ($C_6H_5OC_6H_5$) and the mixture is heated at usually 90 to 130° C. to dissolve the catalyst homogeneously in diphenyl ether. Then, α-olefin or its corresponding alkyl halide is added dropwise in an amount of 0.5 to 1.5 equivalents to one equivalent of diphenyl ether while maintaining 95 to 125° C. for usually 2.5 to 4.5 hours. After completing the dropwise addition, the reaction is conducted at 95 to 125° C. for 5 to 40 minutes. By adding dropwise, it is possible to prevent α-olefin or its corresponding alkyl halide from polymerization such as dimerization. The reaction mixture is allowed to cool to 90° C., then alkali neutralizing agent is added and stirred at 80 to 90° C. for 30 minutes. Then, activated clay is added and the mixture is heated with stirring at 80 to 90° C. for 0.5 to 3 hours. The mixture is allowed to cool to 30° C., then filtered at reduced pressure and distilled at reduced pressure to obtain the diphenyl ether derivative of the formula (3). $R^3$ is a hydrocarbon group having 12 or 14 carbon atoms which is mainly composed by any one of 1-methylundecyl, 1-ethyldecyl, 1-dodecyl, 1-methyltridecyl, 1-ethyldodecyl and 1-tetradecyl, and 30 to 40 mole % of the total benzylic carbons of $R^3$ being quaternary.

Examples of α-olefins are 1-dodecene and 1-tetradecene.

Examples of alkyl halide are 1-dodecyl chloride and 1-tetradecyl chloride.

Generally, in case of reacting a diphenyl ether and α-olefin such as 1-dodecene, theoretically it is considered that mostly 1-methylundecyl group and, as the remainder, 1-ethyldecyl group bond to benzene ring. Namely, it is considered that 1-dodecyl group or a hydrocarbon group wherein the benzylic carbon is quaternary does not bond to benzene ring. However, it is assumed that various reactions occur due to inner isomerization of olefin, and secondary carbon or tertiary carbon are found to exist from the peaks of hydrogen which bond to the benzylic carbons by NMR analysis. The integrated value of the peaks of secondary carbon and tertiary carbon is shortage than the theoretical value and it is considered that quaternary carbon exists. Therefore, in the present invention, addition number of quaternary hydrocarbon group (X) is obtained from the following Analytical Example 1 and this value is defined as ratio of the benzylic carbons being quaternary.

Analytical Example 1

Figure 11:
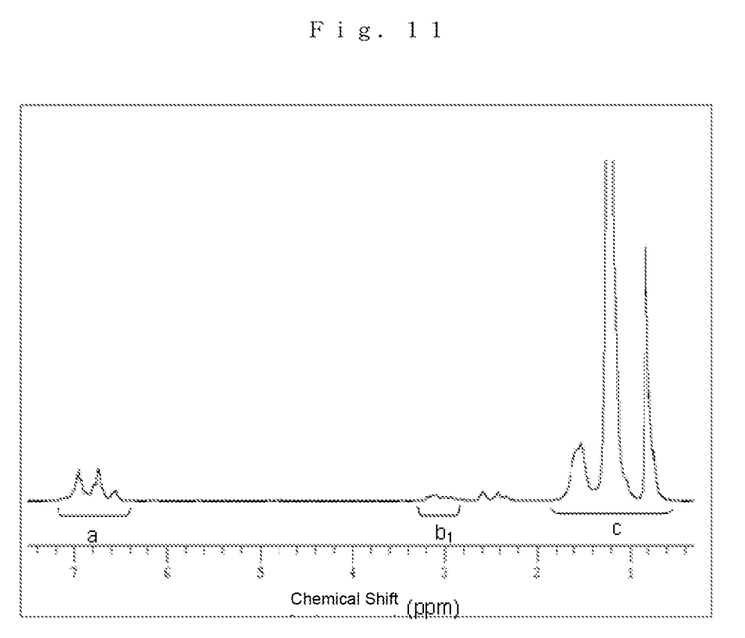
FIG. 11 is $^1$H-NMR spectrum of a model compound.

Calculation of Alkyl Addition Number, and Addition Number of Branched Hydrocarbon Group Wherein the Benzylic Carbon is Quaternary From $^1$H-NMR spectrum of a model compound such as FIG. 11, alkyl addition number, and addition number of branched hydrocarbon group wherein the benzylic carbon is quaternary are calculated.

a (chemical shift 6.5~7.3) shows peak of hydrogen in benzene ring.

b1 (chemical shift 2.8~3.3) and b2 (chemical shift 2.2~2.7) show peak of hydrogen in benzylic position.

c (chemical shift 0.5~1.9) shows peak of hydrogen in alkyl group.

Based on integrated values (ratio) of peaks of a, b1, b2 and c, the addition numbers are calculated by the following equations.

Alkyl addition number$(m+n)=10(b1+b2+c)/[$(average hydrogen number of alkyl group)$a+b1+b2+c]$ In case of $m=1$, Alkyl addition number$(m+n)=1+[\{9(b1+b2+c)-($average hydrogen number of alkyl group $m)a/\{($average hydrogen number of alkyl group $n)a+b1+b2+c\}]$ Addition number of quaternary hydrocarbon group $(X)=(m+n)-[\{b1+(b2 \div 2)\} \times \{10-(m+n)\}]$ Next, a catalyst is added to diphenyl ether derivative of the formula (3) and the mixture is heated at usually 100 to 130° C. to dissolve the catalyst homogeneously in diphenyl ether derivative of the formula (3). Then, a branched α-olefin or its corresponding branched alkyl halide is added dropwise in an amount of 0.5 to 1.5 equivalents to one equivalent of diphenyl ether derivative of the formula (3) while maintaining 110 to 125° C. for usually 2.5 to 4.5 hours. After completing the dropwise addition, the reaction is conducted at 110 to 125° C. for 5 to 40 minutes. By adding dropwise, it is possible to prevent branched α-olefin or its corresponding branched alkyl halide from polymerization such as dimerization. The reaction mixture is allowed to cool to 90° C., then alkali neutralizing agent is added and stirred at 80 to 90° C. for 30 minutes. Then, activated clay is added and the mixture is heated with stirring at 80 to 90° C. for 0.5 to 3 hours. The mixture is allowed to cool to 30° C., then filtered at reduced pressure and distilled at reduced pressure to remove low-boiling compounds, thereby the desired compound of the formula (2) is obtained.

Examples of branched α-olefins are 2-butyloctene, 2-hexyldecene and 2-octyldodecene.

Examples of branched alkyl halides are 2-butyloctyl chloride, 2-hexyldecyl chloride and 2-octyldodecyl chloride.

Generally, in case of reacting a diphenyl ether derivative of the formula (3) and a branched α-olefin of the formula (1), theoretically it is considered that to benzene ring bonds hydrocarbon group wherein all of the benzylic carbons are quaternary. However, it is assumed that various reactions occur due to inner isomerization of olefin, and peaks of hydrogen which bond to the benzylic carbons (secondary carbon or tertiary carbon) are found to exist by NMR analysis. These peaks will not exist when all of the benzylic carbons are quaternary. Therefore, in the present invention, addition number of quaternary hydrocarbon group (X) is obtained similarly from the above Analytical Example 1 and this value is defined as ratio of the benzylic carbons being quaternary.

In the present invention, it is possible to obtain the desired compound of the formula (2) by firstly preparing a diphenyl ether derivative having the substituent $R^4$ added, and then adding the substituent $R^3$ thereto. The reaction is conducted similarly by changing the order of the procedures.

In the compound of the formula (2) of the present invention, m and n are each a real number of $1.0 \le m \le 2.0$ and $1.0 \le n \le 2.0$. Preferably $2.0 \le m+n \le 3.0$. When less than 2.0 in total of m and n, excess amount of evaporation occurs, and when more than 3.0, viscosity and pour point are too high. The compound of the formula (2) may contain monoalkylated diphenyl ether in an amount of about 0.1 to 5 mole %.

In the compound of the formula (2) of the present invention, 42 to 100 mole %, preferably 45 to 95 mole %, more preferably 50 to 90 mole %, particularly preferably 50 to 65 mole % of the total benzylic carbons of each $R^3$ and $R^4$ are quaternary.

The present invention provides a lubricating oil which is usable at high temperature and heat-resistant grease containing a compound of the formula (2)

(2)

wherein $R^3$, $R^4$, m and n are the same as above. The compound of the formula (2) is not limited to one obtained by the present process but those obtained by any process are usable.

To the present lubricating oil can be added, other than the compound of the formula (2), mineral oil, synthetic oils such as α-olefin oligomer, polyol ester, diester, polyalkylene glycol, silicone oil and modified silicone oil. Further, as required, an additive can be added to the present lubricating oil such as anti-wear agent, extreme pressure agent, antioxidant, viscosity index improver, pour point depressant and, rust and corrosion inhibitor. In the present lubricating oil, it is preferable to contain 10 to 99% by weight of the compound of the formula (2), 0 to 90% by weight of mineral oil or synthetic oil, and 1 to 10% by weight of the additive. The present lubricating oil for high temperature can be used as bearing oil, fluid bearing oil, oil-impregnated bearing oil, oil-impregnated plastics oil, gear oil, jet engine oil, adiabatic engine oil, gas turbine oil, automatic transmission fluid, vacuum pump oil and hydraulic fluid which are usable at high temperature.

Further, the present alkyl diphenyl ether can be used as a base oil for grease using lithium hydroxystearate or urea compound as a thickener.

EXAMPLES

The invention will be described in more detail with reference to the following examples and comparative examples to which, however, the invention is not limited. An alkali neutralizing agent used below is Kyoward 1000 [Mg$_{4.5}$·Al$_2$(OH)$_{13}$·CO$_3$· 3.5H$_2$O] of Kyowa Chemical Industry Co., Ltd.

Example 1

Preparation of Compound 1

To a four-necked flask having 20 liter volume equipped with a stirrer, dropping funnel, thermometer and condenser were placed 8000 g (47.1 moles) of diphenyl ether and 30 g (0.23 mole) of anhydrous aluminum chloride. After dissolving anhydrous aluminum chloride with heating at 100° C., to the mixture was added dropwise a mixture of 4260 g (25.4 moles) of 1-dodecene and 4260 g (21.7 moles) of 1-tetradecene while maintaining the temperature at 100° C. for 4.5 hours to perform an addition reaction. After completion of dropwise addition, the mixture was stirred at 100° C. for 30 minutes, then allowed to cool to 90° C., and thereto added 300 g of alkali neutralizing agent and stirred for 30 minutes. To the mixture was added 100 g of activated clay, stirred at 90° C. for one hour and removed aluminum chloride and other acid substances by-produced by filtration at reduced pressure. Then, the resulting product was distilled at reduced pressure of 2.5 to 3.5 torr at 280 to 324° C., thereby 6440 g of monoalkylated diphenyl ether was obtained.

Figure 1:
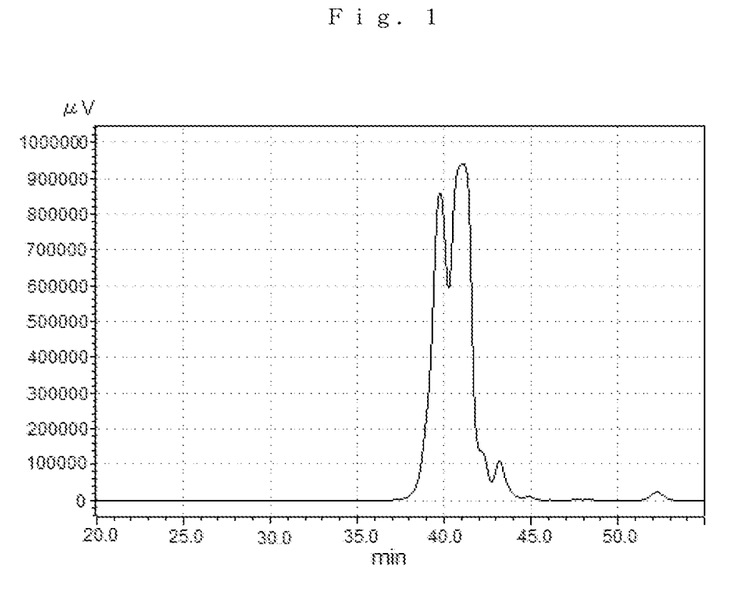
FIG. 1 is GPC spectrum of Compound 1.
Figure 2:
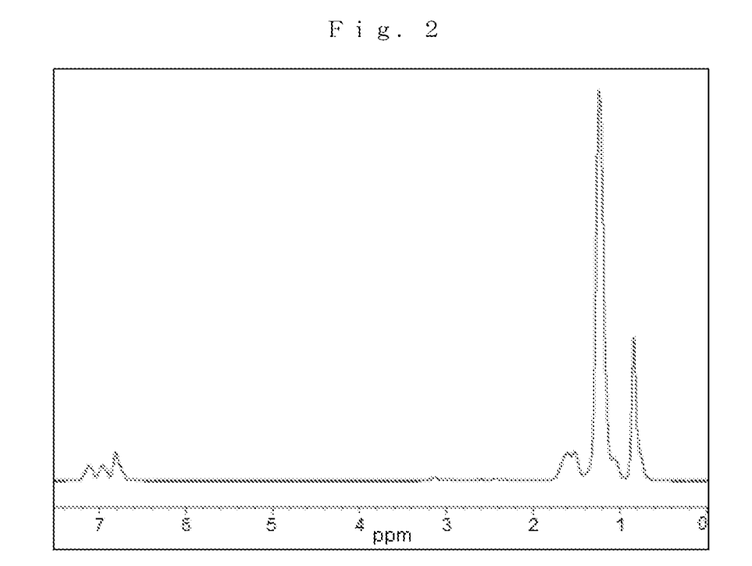
FIG. 2 is $^1$H-NMR spectrum of Compound 1.

Next, to a four-necked flask having 10 liter volume equipped with a stirrer, dropping funnel, thermometer and condenser were placed 4500 g (12.8 moles) of monoalkylated diphenyl ether obtained above and 18 g (0.14 mole) of anhydrous aluminum chloride. After dissolving anhydrous aluminum chloride with heating at 110° C., to the mixture was added dropwise 2500 g (8.9 moles) of 2-octyldodecene while maintaining the temperature at 110° C. for 4.5 hours to perform an addition reaction. After completion of dropwise addition, the mixture was stirred at 110° C. for 30 minutes, then allowed to cool to 90° C., and thereto added 180 g of alkali neutralizing agent and stirred for 30 minutes. To the mixture was added 90 g of activated clay, stirred at 90° C. for one hour and removed aluminum chloride and other acid substances by-produced by filtration at reduced pressure. Then, removing unreacted starting material and monoalkylated diphenyl ether by distillation at reduced pressure of 2.5 to 3.5 torr at 250 to 324° C., thereby 4480 g of alkyl diphenyl ether wherein dialkylated diphenyl ether was contained as a main component was obtained. The product (referred to as Compound 1) was 2.23 in alkyl addition number from GPC spectrum (FIG. 1) and $^1$H-NMR spectrum (FIG. 2). The ratio of the benzylic carbons being quaternary was 53.0 mole %.

GPC
Retention time of monoalkylated diphenyl ether: 42.736~44.597 3.35 mole %
Retention time of dialkylated diphenyl ether: 40.260~42.736 57.3 mole %
Retention time of trialkylated diphenyl ether: 37.069~40.260 39.3 mole %
$^1$H-NMR (solvent: none, standard substance: none)
Integrated value of δ=6.5~7.3 ppm is 1,
integrated value of δ=2.8~3.3 ppm is 0.10,
integrated value of δ=2.2~2.7 ppm is 0.07,
integrated value of δ=0.5~1.9 ppm is 9.80.

GPC system of Shimadzu Corp. was used. The system was as follows. CBM-20A (system controller), DGU-20A3 (online degasser for three channels), LC-20AD (liquid feed unit for high-precision analysis), SIL-20A (auto-sampler), RID-10A (refractive index detector) and SPD-20A (UV-VIS detector).

In the measurement, three KF-803L columns, THF (mobile phase) and SPD-20A (detector) were used. Flow rate was 30 MPa.

$^1$H-NMR was measured by using a nuclear magnetic resonance device, JNM-ECX400 of JEOL Ltd. at 80° C. without solvent and standard substance.

Chemical shift was obtained by conducting the measurement using the same compound, deuterated chloroform as solvent and TMS as standard substance. This is why peaks of deuterated chloroform overlap with those of benzene ring and precious integrated values are unavailable.

The ratio of each alkyl-adducted compound such as monoalkyl-adducted compound was calculated from each peak area of GPC spectrum. In case a peak is not an independent peak, the ratio was calculated from each peak area obtained by drawing a perpendicular line from valley of neighboring two peaks.

Example 2

Preparation of Compound 2

Figure 3:
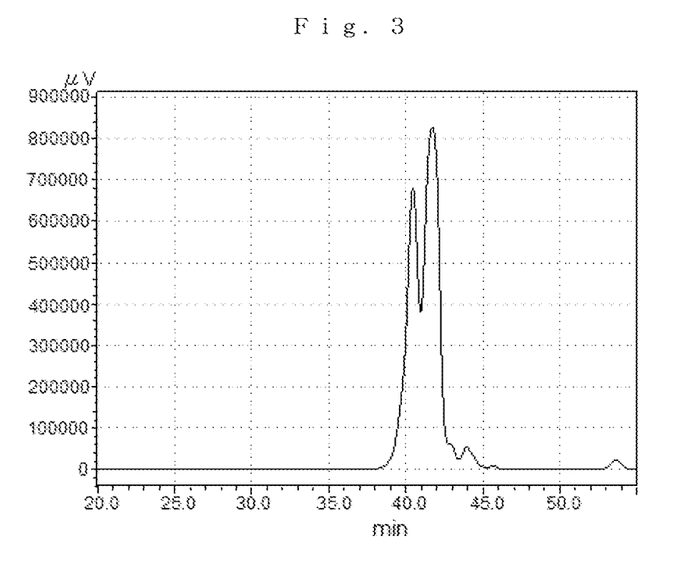
FIG. 3 is GPC spectrum of Compound 2.
Figure 4:
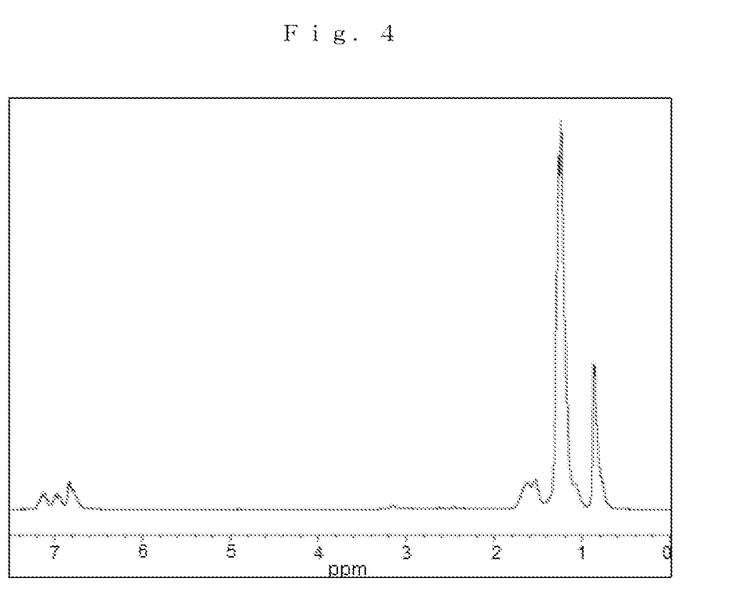
FIG. 4 is $^1$H-NMR spectrum of Compound 2.

The experiment was conducted in the same manner as in Example 1 except that 4500 g (12.8 moles) of monoalkylated diphenyl ether obtained in Example 1, 20 g (0.15 mole) of anhydrous aluminum chloride, 2860 g (10.2 moles) of 2-octyldodecene, 200 g of alkali neutralizing agent and 100 g of activated clay were used in a four-necked flask having 10 liter volume to obtain 5050 g of alkyl diphenyl ether wherein dialkylated diphenyl ether was contained as a main component. The product (referred to as Compound 2) was 2.28 in alkyl addition number from GPC spectrum (FIG. 3) and $^1$H-NMR spectrum (FIG. 4). The ratio of the benzylic carbons being quaternary was 54.3 mole %.

GPC
Retention time of monoalkylated diphenyl ether: 43.441~45.191 2.63 mole %
Retention time of dialkylated diphenyl ether: 40.964~43.441 57.6 mole %
Retention time of trialkylated diphenyl ether: 36.474~40.964 39.8 mole %
$^1$H-NMR (solvent: none, standard substance: none)
Integrated value of δ=6.5~7.3 ppm is 1,
integrated value of δ=2.8~3.3 ppm is 0.10,
integrated value of δ=2.2~2.7 ppm is 0.07,
integrated value of δ=0.5~1.9 ppm is 10.13.

Example 3

Preparation of Compound 3

Figure 5:
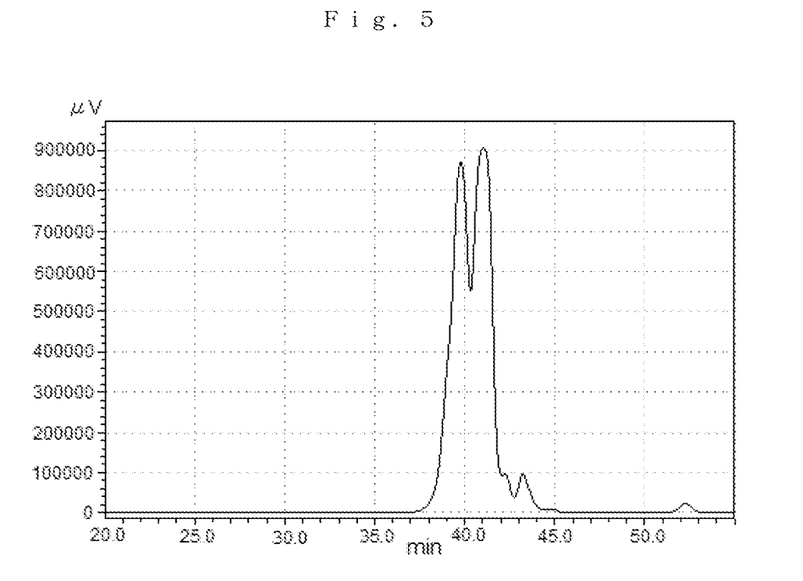
FIG. 5 is GPC spectrum of Compound 3.
Figure 6:
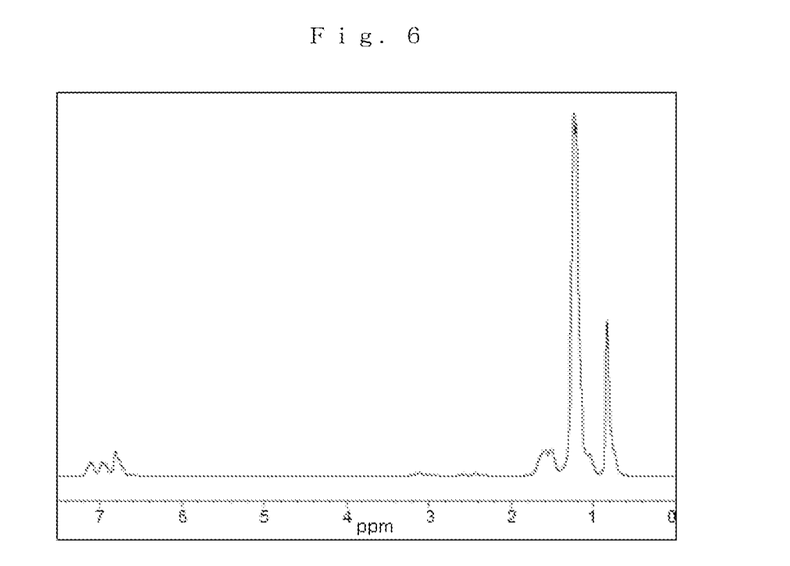
FIG. 6 is $^1$H-NMR spectrum of Compound 3.

The experiment was conducted in the same manner as in Example 1 except that 4500 g (12.8 moles) of monoalkylated diphenyl ether obtained in Example 1, 25 g (0.19 mole) of anhydrous aluminum chloride, 3580 g (12.8 moles) of 2-octyldodecene, 250 g of alkali neutralizing agent and 125 g of activated clay were used in a four-necked flask having 10 liter volume to obtain 5980 g of alkyl diphenyl ether wherein dialkylated diphenyl ether was contained as a main component. The product (referred to as Compound 2) was 2.37 in alkyl addition number from GPC spectrum (FIG. 5) and $^1$H-NMR spectrum (FIG. 6). The ratio of the benzylic carbons being quaternary was 51.8 mole %.

GPC
Retention time of monoalkylated diphenyl ether: 42.774~44.616 3.06 mole %
Retention time of dialkylated diphenyl ether: 40.332~42.774 50.3 mole %
Retention time of trialkylated diphenyl ether: 37.055~40.332 46.6 mole %
$^1$H-NMR (solvent: none, standard substance: none)
integrated value of δ=6.5~7.3 ppm is 1,
integrated value of Δ=2.8~3.3 ppm is 0.11,
integrated value of δ=2.2~2.7 ppm is 0.08,
integrated value of δ=0.5~1.9 ppm is 10.73.

Example 4

Preparation of Compound 4

Figure 7:
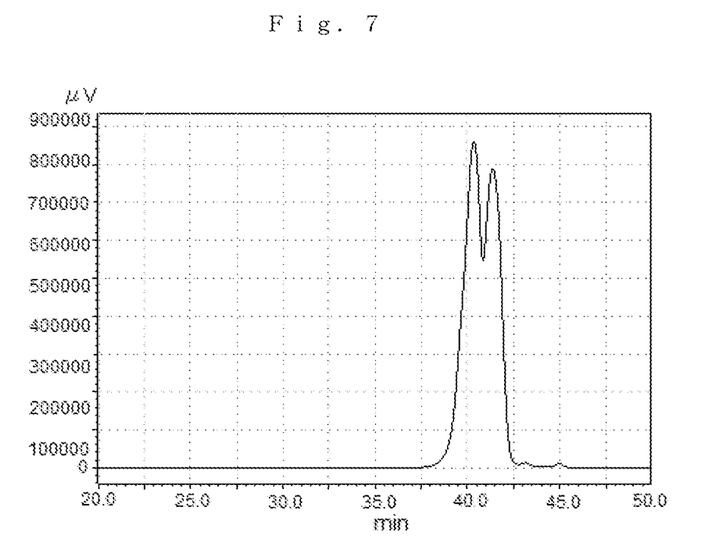
FIG. 7 is GPC spectrum of Compound 4.
Figure 8:
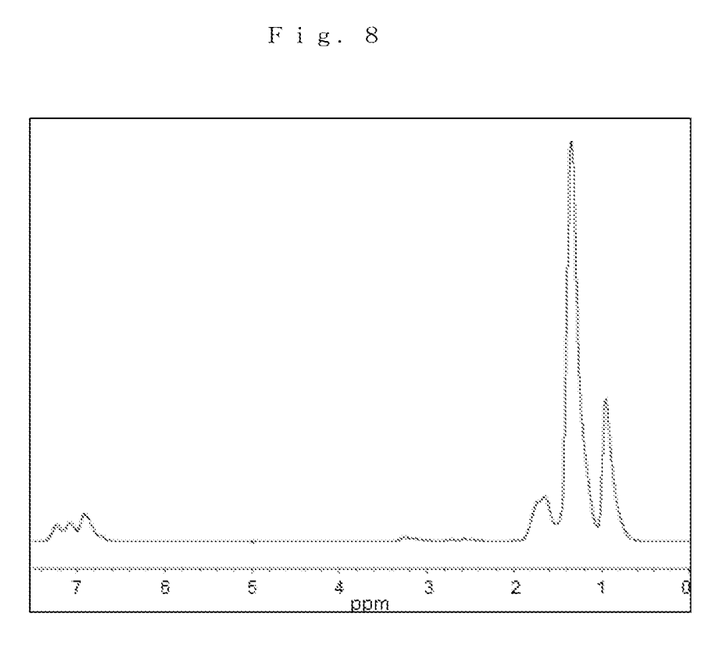
FIG. 8 is $^1$H-NMR spectrum of Compound 4.

The experiment was conducted in the same manner as in Example 1 except that 400 g (1.14 moles) of monoalkylated diphenyl ether obtained in Example 1, 2.5 g (0.19 mole) of anhydrous aluminum chloride, 360 g (1.60 moles) of 2-hexyldecene, 25 g of alkali neutralizing agent and 12 g of activated clay were used in a four-necked flask having one liter volume to obtain 510 g of alkyl diphenyl ether wherein dialkylated diphenyl ether was contained as a main component. The product (referred to as Compound 4) was 2.41 in alkyl addition number from GPC spectrum (FIG. 7) and ¹H-NMR spectrum (FIG. 8). The ratio of the benzylic carbons being quaternary was 54.4 mole %.
GPC
Retention time of monoalkylated diphenyl ether: 42.773~43.761 0.4 mole %
Retention time of dialkylated diphenyl ether: 40.850~42.773 44.8 mole %
Retention time of trialkylated diphenyl ether: 37.206~40.850 54.8 mole %
¹H-NMR (solvent: none, standard substance: none)
Integrated value of δ=6.5~7.3 ppm is 1,
integrated value of δ=2.8~3.3 ppm is 0.09,
integrated value of δ=2.2~2.7 ppm is 0.11,
integrated value of δ=0.5~1.9 ppm is 10.29.

Comparative Example 1

Preparation of Compound 5

Figure 9:
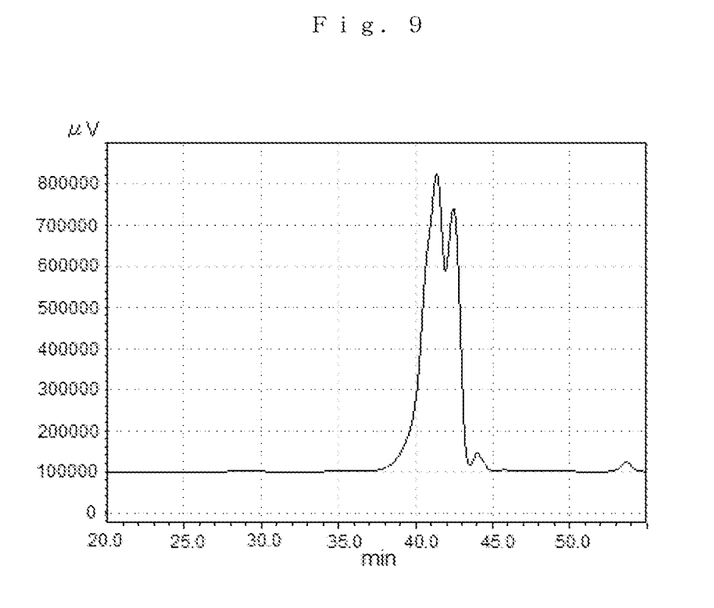
FIG. 9 is GPC spectrum of Compound 5.
Figure 10:
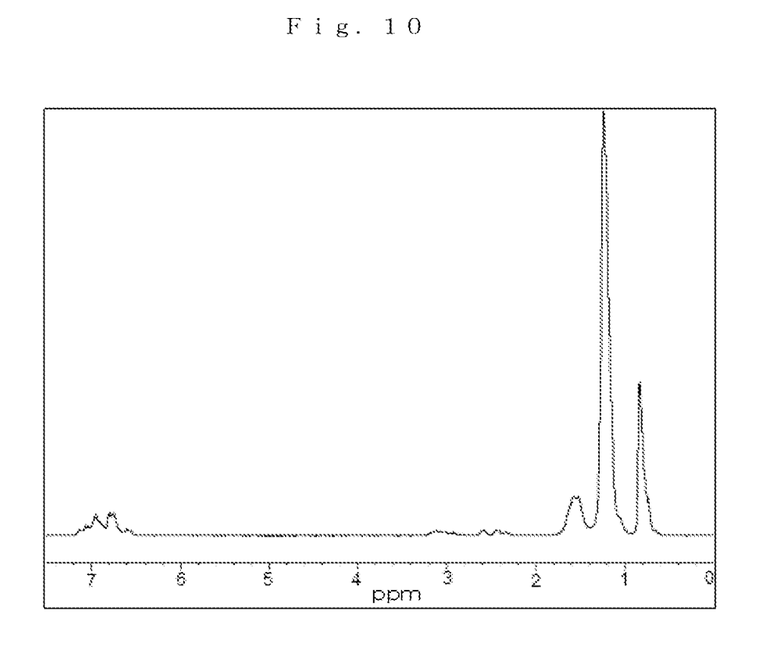
FIG. 10 is $^1$H-NMR spectrum of Compound 5.

To the same flask used in Example 1 were placed 1600 g (9.4 moles) of diphenyl ether and 15 g (0.11 mole) of anhydrous aluminum chloride. After dissolving anhydrous aluminum chloride with heating at 110° C., to the mixture was added dropwise a mixture of 1810 g (10.8 moles) of 1-dodecene and 1810 g (9.23 moles) of 1-tetradecene under nitrogen stream while maintaining the temperature at 110° C. for 4.5 hours to perform an addition reaction. After completion of dropwise addition, the mixture was stirred at 110° C. for 30 minutes, then allowed to cool to 90° C., and thereto added 68 g of alkali neutralizing agent and stirred for 30 minutes. To the mixture was added 68 g of activated clay, stirred at 90° C. for one hour and removed aluminum chloride and other acid substances by-produced by filtration at reduced pressure. Then, removing unreacted starting material and monoalkylated diphenyl ether by distillation at reduced pressure of 3.0 to 4.0 torr at 250 to 320° C., thereby 6000 g of alkyl diphenyl ether wherein dialkylated diphenyl ether was contained as a main component was obtained. The product (referred to as Compound 4) was 2.82 in alkyl addition number from GPC spectrum (FIG. 9) and ¹H-NMR spectrum (FIG. 10). The ratio of the benzylic carbons being quaternary was 37.8 mole %.
GPC
Retention time of monoalkylated diphenyl ether: 43.766~45.224 1.8 mole %
Retention time of dialkylated diphenyl ether: 42.157~43.766 34.2 mole %
Retention time of trialkylated diphenyl ether: 37.328~42.157 64.0 mole % integrated value of δ=6.5~7.3 ppm is 1,
integrated value of δ=2.8~3.3 ppm is 0.16,
integrated value of δ=2.2~2.7 ppm is 0.17,
integrated value of δ=0.5~1.9 ppm is 10.30.

Example 5

Preparation of Heat-Resistant Grease Composition

To a glass vessel were added Compound 1 (230 g) obtained in Example 1 and 70 g of p-toluidine and the mixture was heated at 70 to 80° C. with stirring to obtain Solution A. To an another glass vessel were added Compound 1 (230 g) and 57 g of tolylene diisocyanate and the mixture was heated at 70 to 80° C. with stirring to obtain Solution B. To Solution A in a separable flask was added gradually Solution B over about 30 minutes with stirring. The mixture was heated until 170° C. with stirring for 40 minutes to obtain grease (Composition 1) containing urea compound as a thickener.

Test Example 1

Heat Stability Test

In 30-ml glass beaker was weighed 20 g of each Compounds 1 to 5. Each sample was allowed to place in a thermostatic oven of 200° C. After 10 days or 20 days, the sample was checked for weight, kinematic viscosity and acid value. Change of properties by heat stability test was evaluated based on the values measured before the test.

Test Example 2

Fluidity at Low Temperature Test

Compounds 1 to 9 were checked for pour point according to JIS K2269.

Test Example 3

Lubricity Test

Friction coefficient was measured under a load of 0.98N and while raising the sample temperature from 25° C. to 250° C. by Ball on Plate friction tester using SUJ2 steel as Ball and SK-5 steel as Plate.
Table 1 shows the general properties, Table 2 the results of heat stability test, and Table 3 the results of lubricity test of Compounds 1 to 5. Table 4 shows oil separation of the grease composition prepared in Example 5.

TABLE 1

|  | Compound 1 Example 1 | Compound 2 Example 2 | Compound 3 Example 3 | Compound 4 Example 4 | Compound 5 Com. Ex.1 |
|---|---|---|---|---|---|
| alkyl group | $R^3 + R^4$ | $R^3 + R^4$ | $R^3 + R^4$ | $R^3 + R^4$ | $R^3$ |
| alkyl addition mole number | 2.23 | 2.28 | 2.37 | 2.41 | 2.82 |
| Properties |  |  |  |  |  |
| 40° C. kinematic viscosity (mm²/s) | 123.2 | 127.1 | 134.1 | 122.6 | 102.6 |
| 100° C. kinematic viscosity (mm²/s) | 13.96 | 14.32 | 14.97 | 13.98 | 12.60 |
| viscosity index | 111 | 112 | 113 | 112 | 116 |
| pour point (° C.) | −45 | −4 | −45 | −45 | −45 |

Table 1 confirms Compounds 1 to 4 of the present invention exhibit low pour point equal to Compound 5 which is a conventional compound.

TABLE 2

|  | Compound 1 Example 1 | Compound 2 Example 2 | Compound 3 Example 3 | Compound 4 Example 4 | Compound 5 Com. Ex.1 |
|---|---|---|---|---|---|
| evaporation loss rate (%) 200° C. after 20 days | 15.7 | 15.6 | 14.4 | 15.3 | 20.0 |
| viscosity ratio (times) 200° C. after 20 days | 7.8 | 7.2 | 7.0 | 7.3 | 8.8 |
| acid value (mgKOH/g) before exam. | 0.00 | 0.01 | 0.01 | 0.01 | 0.01 |
| 200° C. after 20 days | 5.78 | 5.95 | 5.57 | 5.67 | 7.58 |

From the results of Table 2, it is confirmed that Compounds 1 to 4 of the present invention exhibit low evaporation loss rate, low viscosity ratio and low in increase of acid value compared with Compound 5 which is known as a lubricant for high temperature.

TABLE 3

|  | Compound 1 Example 1 | Compound 2 Example 2 | Compound 3 Example 3 | Compound 4 Example 4 | Compound 5 Com. Ex.1 |
|---|---|---|---|---|---|
| friction coefficient (150° C.) | 0.1605 | 0.1586 | 0.1607 | 0.1610 | 0.1723 |

Table 3 confirms Compounds 1 to 4 of the present invention exhibit low friction coefficient and are suitable for various lubricants compared with Compound 5 which is a conventional compound.

TABLE 4

|  | Example 5 Composition 1 |
|---|---|
| base oil | Compound 1 |
| thickener | Urea compound |
| oil separation (100° C., 24 H, % | 0.4 |

Table 4 confirms the grease composition (Composition 1) using Compound 1 of the present invention as a base oil and urea compound as a thickener is less than 1% in oil separation and is practically suitable for grease.

From the above, the present compound exhibits fluidity at low temperature equal to a conventionally well-known and practically used alkylated diphenyl ether. Further, the present compound is low in evaporation amount in heat stability test and is suppressed in increase of acid value compared with a conventional alkylated diphenyl ether which is widely used as a base oil for a lubricant for high temperature and heat-resistant grease.

The base oil for a lubricant for high temperature and heat-resistant grease is most required to be suppressed in increase of acid value. Therefore, the present compound is confirmed to be excellent in heat resistance compared with a conventional alkylated diphenyl ether.

INDUSTRIAL APPLICABILITY

The present compound and composition are not only usable as a base oil for various lubricants such as bearing oil, fluid bearing oil, oil-impregnated bearing oil, oil-impregnated plastics oil, gear oil, engine oil, gas turbine oil, automatic transmission fluid, vacuum pump oil, other machine oil and hydraulic fluid, but also usable as a base oil for grease. Further, the present compound can be added to or used conjointly with other synthetic base oil, and is suitable to expand design width of lubricants. In addition, the present compound is not only usable as lubricants but also as plasticizer, refrigerating oil or the like.

The invention claimed is:

1. A mixture consisting essentially of compounds having the formula (2)

(2)

wherein $R^3$ is a hydrocarbon group having 12 or 14 carbon atoms, and 30 to 40 mole % of the total benzylic carbons of $R^3$ being quaternary, $R^4$ is a branched hydrocarbon group having 16 to 20 carbon atoms, 42 to 100 mole % of the total benzylic carbons of each $R^3$ and $R^4$ being quaternary, m and n are each a real number of $1.0 \leq m \leq 2.0$, $1.0 \leq n \leq 2.0$ and $2.0 \leq m+n \leq 3.0$, and monoalkylated diphenyl ether in an amount of about 0.1 to 5 mole % of the mixture.

2. A mixture consisting essentially of compounds having the formula (2) obtained by an addition reaction of diphenyl ether derivative of the formula (3) and a branched α-olefin of the formula (1) or its corresponding branched alkyl halide wherein $R^1$ and $R^2$ are the same or different and are a hydrocarbon group having 4 to 12 carbon atoms, $R^3$ is a hydrocarbon group having 12 or 14 carbon atoms, and 30 to 40 mole % of the total benzylic carbons of $R^3$ being quaternary, $R^4$ is a branched hydrocarbon group having 16 to 20 carbon atoms, 42 to 100 mole % of the total benzylic carbons of each $R^3$ and $R^4$ being quaternary, m and n are each a real number of $1.0 \leq m \leq 2.0$, $1.0 \leq n \leq 2.0$ and $2.0 \leq m+n \leq 3.0$, and monoalkylated diphenyl ether in an amount of about 0.1 to 5 mole % of the mixture.

3. The mixture as defined in claim 1 wherein the total of a ratio of the carbon at benzyl position of each $R^3$ and $R^4$ being quaternary is 45 to 95 mole %.

4. The mixture as defined in claim 1 wherein 50 to 90 mole % of the total benzylic carbons of each $R^3$ and $R^4$ is quaternary.

5. The mixture as defined in claim 1 wherein 50 to 65 mole % of the total benzylic carbons of each $R^3$ and $R^4$ is quaternary.

6. The mixture as defined in claim 1 wherein $R^4$ is 1-butyl-1-methylheptyl, 1-methyl-1-pentyloctyl, 1-hexyl-1-methylnonyl, 1-heptyl-1-methyldecyl, 1-methyl-1-octylundecyl or 1-decyl-1-methyltridecyl.

7. A lubricating oil containing the mixture of claim 1.

8. A grease containing the mixture of claim 1.

9. A grease composition as defined in claim 8 wherein the grease composition is used for bearing.

10. A mixture consisting essentially of compounds having formula (2) obtained by an addition reaction of diphenyl ether derivative of the formula (4) and an α-olefin of the formula (5) or (6)

wherein $R^3$ is a hydrocarbon group having 12 or 14 carbon atoms, and 30 to 40 mole % of the total benzylic carbons of $R^3$ being quaternary, $R^4$ is a branched hydrocarbon group having 16 to 20 carbon atoms, 42 to 100 mole % of the total benzylic carbons of each R3 and R4 being quaternary, m and n are each a real number of $1.0 \leq m \leq 2.0$, $1.0 \leq n \leq 2.0$ and $2.0 \leq m+n \leq 3.0$, and monoalkylated diphenyl ether in an amount of about 0.1 to 5 mole % of the mixture.

11. The mixture as defined in claim 1 wherein $2.0 \leq m+n \leq 2.5$.

12. The mixture as defined in claim 11 wherein $2.23 \leq m+n \leq 2.41$.

13. A mixture consisting essentially of compounds having the formula (2)

wherein $R^3$ is a hydrocarbon group having 12 or 14 carbon atoms which is composed of any one of 1-methylundecyl, 1-ethyldecyl, 1-dodecyl, 1-methyltridecyl, 1-ethyldodecyl or 1-tetradecyl, $R^3$ further comprises a hydrocarbon group having 12 or 14 carbon atoms wherein the benzylic carbon is quaternary, and 30 to 40 mole % of the total benzylic carbons of $R^3$ being quaternary, $R^4$ is a branched hydrocarbon group having 16 to 20 carbon atoms, 42 to 100 mole % of the total benzylic carbons of each $R^3$ and $R^4$ being quaternary, m and n are each a real number of $1.0 \leq m \leq 2.0$, $1.0 \leq n \leq 2.0$ and $2.0 \leq m+n \leq 3.0$, and monoalkylated diphenyl ether in an amount of about 0.1 to 5 mole % of the mixture.

* * * * *